United States Patent [19]
Sakai

[11] Patent Number: 5,455,037
[45] Date of Patent: Oct. 3, 1995

[54] ERYTHROMYCIN CREAM

[75] Inventor: Kirk Sakai, Margate, Fla.

[73] Assignee: Stiefel Laboratories, Inc., Coral Gables, Fla.

[21] Appl. No.: 350,661

[22] Filed: Dec. 7, 1994

[51] Int. Cl.⁶ .................................................. A61K 7/40
[52] U.S. Cl. ........................................ 424/401; 514/887
[58] Field of Search ............................ 424/401; 514/887

[56] References Cited

U.S. PATENT DOCUMENTS

| 4,497,794 | 2/1985 | Klein et al. | 424/81 |
| 4,692,329 | 9/1987 | Klein et al. | 424/81 |
| 5,132,443 | 7/1992 | Traver et al. | 556/425 |
| 5,292,530 | 3/1994 | McCrea et al. | 424/66 |
| 5,322,689 | 6/1994 | Hughes et al. | 424/401 |

OTHER PUBLICATIONS

Chemical Abstract 116: 158932. 1995.
Matschiner et al. (1994) *Proceed. Intern. Symp. Control. Rel. Bioact. Mater,* vol. 21, pp. 698–699.

*Primary Examiner*—Thurman K. Page
*Assistant Examiner*—Sharon Howard
*Attorney, Agent, or Firm*—Mathews, Woodbridge & Collins

[57] ABSTRACT

Dermal microbial infections in animals are treated with a topical cream composition comprising about 3 to 4% erythromycin in an emulsion.

6 Claims, No Drawings

ERYTHROMYCIN CREAM

The present invention pertains to topical cream compositions and methods for treating dermal microbial infections in animals.

Numerous microbial infections afflict the dermis of animals. Microbial skin diseases include acne, cystic acne, acne vulgaris rosacea, and dermatitis herpetiformis. In addition, other common dermal infections include those caused by gram positive and gram negative organisms.

Preparations including erythromycin have been proposed to treat these afflictions. These preparations include erythromycin and benzoyl peroxide in gel form which are generally combined immediately prior to use, since the two active agents are relatively incompatible and unstable. After combining the two agents, the mixtures must be used within 24 hours, otherwise refrigeration is required. After three months of refrigeration, the compositions lose potency and must be discarded. In addition, these formulations generally have a high content of alcohol, known to be drying to the skin.

The present invention pertains to topical cream compositions and methods for treating dermal microbial infections in animals. The compositions are highly stable and effective in a cosmetically elegant form comprising erythromycin in an emulsion which is high in water content and low in alcohol content.

In particular, the topical cream compositions comprise from about 3% to about 4% by weight of the total composition of erythromycin in an emulsion comprising (i) at least one polysiloxane, (ii) about 11–12% of ethanol, (iii) at least 50% water, and (iv) at least one emulsifier. The compositions maintain stability for at least three months at ambient temperature despite the relative instability of erythromycin.

This invention also relates to methods for treating dermal microbial infections which comprise topically applying to at least the affected area an effective amount of the composition.

Referring to the active ingredient, erythromycin is an antibiotic substance produced by a strain of *Streptomycis erythreus*. Several forms of erythromycin exist. The present composition and methods are not limited to employing a particular form and, in the alternative, can include the pharmaceutically acceptable salts of erythromycin if desired.

The emulsion comprises the following components: (i) at least one polysiloxane; (ii) about 11% to 12% by weight of the composition ethanol; (iii) at least 50% by weight of the total composition of water; and (iv) at least one emulsifier.

Referring to the first component, polysiloxanes are preferably cyclomethicone, dimethicone, and dimethicone copolyol. Alternatively, other typical polysiloxanes include a series of branched silicones: cycloethoxymethicone, cyclic dimethyl polysiloxane, and cyclic ethoxymethyl polysiloxane. Representative dimethicone copolyols include dimethicone copolyol acetate, adipate, amine, behenate, butyl ether, hydroxystearate, isostearate, laurate, methyl ether, phosphate, and stearate. Additionally, the polysiloxane can be dimethicone propyl ether or dimethicone propyl PG-betaine. Preferably, the amount of polysiloxanes present in the compositions and methods is from about 5% to 6% based on the weight of the total composition.

Referring to the second component, alcohol is present in the compositions and methods ranging from about 11% to about 12% of ethanol based on the weight of the total composition. The third component of the emulsion is water. At least 50% of water is present in the compositions and methods, again based on the weight of the total composition.

The emulsifier as the fourth component preferably comprises a mixture of at least one fatty acid alcohol, at least one polyoxyethylene ether, and at least one diethanolamine salt. As the first component of the mixture, representative fatty acid alcohols include those alcohols having an alkyl chain, either straight or branched and having from 10 to 22 carbon atoms. Preferably, there are 18 carbon atoms in the alcohol, i.e., octadecanol. The second components are polyoxyethylene ethers which preferably comprise steareth 2 and steareth 21. However, the length of the ethylene oxide chain can range between 2 and 100. The third component is at least one diethanolamine salt. Typical diethanolamine (DEA) salts include DEA-cetyl phosphate and DEA cetyl sulfate. Preferably, DEA-cetyl phosphate is employed.

The foregoing ingredients are mixed to produce the composition, in addition to auxiliary ingredients for pH adjustment, thickening, and preserving of the composition. Generally, the pH is adjusted with triethanolamine, or any suitable agent. The thickener can be, for example, xanthan gum and the like. Hydroxybenzoates such as methylparaben and butylparaben are used as preservatives in an effective amount, although other conventional preservatives such as imidurea and phenoxyethanol can also be employed. Additional auxiliary ingredients such as fragrances and colorants can also be added.

The resultant formulation is suitable for use on the animal dermis for effectively treating microbial infections. Advantageously, the composition is stable, high in water content, low in alcohol content, and does not cause irritation to the skin of animals. The emulsion containing the combination of at least one silicon-based polysiloxane, at least one fatty acid alcohol, and at least one diethanolamine salt contributes to the stability of the product, which is maintained for at least three (3) months at ambient or room temperature without the need for refrigeration, thus freeing the user from the refrigerator. In addition, chemical stability is maintained indefinitely when the composition is refrigerated at about 2° C. to 8° C. temperatures. Thus, the cream formulation has improved physical attributes over other erythromycin formulations at refrigerated, ambient, and elevated temperatures.

The cream compositions according to the present invention are topically applied to at least the affected area once or twice daily. However, since the compositions of the present invention typically are used under a physician's care, the precise treatment regimen in each case will be determined by the physician based upon the exact diagnosis, the severity of the condition, concurrent use of other therapeutic agents, responsiveness to treatment, tolerance of treatment, and other related medical considerations.

The following example will serve to further typify the nature of the invention but should not be construed as a limitation on the scope thereof which is defined solely by the appended claims.

EXAMPLE 1

A topical cream is prepared by combining the following components:

a) In a suitable container, mix the following ingredients until homogeneous:

| Ingredient Water Phase | Parts by Weight |
|---|---|
| Purified water | 53.13% |
| Carbomer | 0.200% |
| Xanthan gum | 0.200% |
| Propylene glycol | 3.00x% |
| Dimethicone copolyol | 1.00x% |
| Disodium EDTA | 0.050% |
| Methylparaben | 0.300% |
| Premix of triethanolamine and water | 0.200% 1.00x% |
| Total: | 59.08% |

In the first container, the purified water, carbomer, and xanthan gum are heated to about 70° C. Thereafter, propylene glycol, dimethicone copolyol, disodium EDTA, and methylparaben are added. The pre-mix is slowly added to the mixture.

b) In a second suitable container the following ingredients are combined:

| Ingredient Oil Phase: | Parts by Weight |
|---|---|
| Mineral oil, light | 6.75x% |
| Cyclomethicone | 3.00x% |
| Dimethicone | 1.25x% |
| Stearyl alcohol | 5.40x% |
| Steareth-21 | 5.40x% |
| Steareth | 3.60x% |
| Diethanolamine-cetyl phosphate | 0.30x% |
| Butylparaben | 0.07x% |
| Total: | 25.77% |

In the second container, the ingredients are heated to about 70°–75° C. and mixing is begun as the ingredients begin to melt. When the temperature of the oil phase reaches about 70°–75° C., add the oil phase to the water phase in the first container, and allow to cool to room temperature while mixing continues.

c) In a third suitable container, mix the following ingredients to form a solution:

| Ingredient Solution: | Parts by Weight |
|---|---|
| Solvent/diluent SD Alcohol 40 | 12.00x% |
| Active ingredient | 3.15x% |
| Erythromycin | |
| Total: | 15.15% |
| Total composition: | 100% |

Warm the solution if the active ingredient does not dissolve within about 3–5 minutes. When the temperature of the cream reaches 38°–40° C., add the erythromycin-alcohol solution. Mix until homogeneous.

The resulting cream remains stable after standing for at least three months at ambient temperature and relative humidity.

What is claimed is:

1. A stable topical cream composition for treating dermal microbial infections in an animal, comprising:

from about 3% to about 4% by weight of the total composition of erythromycin in an emulsion comprising:
  (i) a polysiloxane or mixture thereof,
  (ii) about 11% to 12% by weight of the total composition of ethanol,
  (iii) at least 50% by weight of the total composition of water, and
  (iv) an emulsifier or mixture thereof, wherein the composition is stable for at least three months at ambient temperature.

2. The composition according to claim 1 wherein the emulsifier comprises a mixture of a fatty acid alcohol, a polyoxyethylene ether, and a diethanolamine salt.

3. The composition according to claim 2 wherein the emulsifier comprises a mixture of octadecanol, steareth 2, steareth 21 and diethanolamine cetyl phosphate.

4. The composition according to claim 1 wherein the polysiloxane is (i) cyclomethicone, (ii) dimethicone, or (iii) dimethicone copolyol.

5. The composition according to claim 4 wherein the polysiloxane is a mixture of (i) cyclomethicone, (ii) dimethicone, and (iii) dimethicone copolyol.

6. A method of treating skin diseases associated with dermal microbial infections in an animal, comprising applying to at least the affected area an effective amount of the composition of claim 1.

* * * * *